United States Patent [19]

Kaul et al.

[11] 4,235,864

[45] Nov. 25, 1980

[54] SIMULTANEOUS RADIO IMMUNOASSAY OF MULTIPLE ANTIGENS AND ASSAY FOR COCAINE METABOLITES

[75] Inventors: Balkrishena Kaul, West Caldwell, N.J.; Bernard Davidow, Flushing, N.Y.; Stephen J. Millian, East Brunswick, N.J.

[73] Assignee: Research Corporation, N.Y.

[21] Appl. No.: 895,020

[22] Filed: Apr. 10, 1978

Related U.S. Application Data

[62] Division of Ser. No. 761,078, Jan. 21, 1977.

[51] Int. Cl.$^2$ .................... G01N 33/16; A61K 43/00; A61K 39/00
[52] U.S. Cl. ........................................ 424/1; 424/12; 260/112 B
[58] Field of Search .............................. 546/129–132; 260/112 B; 424/112, 1; 23/230 B

[56] References Cited

U.S. PATENT DOCUMENTS

| | | | |
|---|---|---|---|
| 3,917,582 | 11/1975 | Soffer et al. | 546/130 |
| 3,966,764 | 6/1976 | Goldstein et al. | 546/129 |
| 4,041,040 | 8/1977 | Christenson et al. | 546/130 |
| 4,045,420 | 8/1977 | Soffer et al. | 546/130 |
| 4,071,522 | 1/1978 | Christenson et al. | 424/1 |
| 4,102,979 | 7/1978 | Christenson | 546/131 |

OTHER PUBLICATIONS

Cleeland et al, Clin. Chem., vol. 22., No. 6, 1976, pp. 712–725.
Mule et al, Clin. Chem., vol. 21, No. 1, 1975, pp. 81–86.
Usategui-Gomez et al, Clin. Chem., vol. 21, No. 10, 1975, pp. 1378–1382.

*Primary Examiner*—Benjamin R. Padgett
*Assistant Examiner*—Christine M. Nucker
*Attorney, Agent, or Firm*—Dennis P. Clarke

[57] ABSTRACT

This invention includes an antigenic conjugate of ecgonine and a carrier which elicits anti-benzoylecgonine (cocaine metabolite) serum useful for the detection of cocaine metabolites in human organs and body fluids by immunoassay. The invention also includes the method of producing the anti-benzoylecgonine serum, the immunoassay method and composition including the anti-benzoylecgonine serum and a labeled benzoylecgonine and a non-labeled benzoylecgonine.

The invention also includes a composition comprising a plurality of antigenic conjugates which elicit a multivalent anti-serum capable of complexing a plurality of antigens in a multiple immunoassay detection method. The invention includes the method of producing the multivalent anti-serum and an immunoassay method employing the multivalent anti-serum. The invention further includes a composition comprising the multivalent anti-serum and a plurality of labeled antigens and non-labeled antigens.

9 Claims, 12 Drawing Figures

Relative binding of cocaine, benzoylecgonine and ecgonine to ecgonine-SGG antiserum. Cocaine (▲——▲); norcocaine (□——□); benzoylecgonine (●——●); benzoylnorecgonine (△——△); ecgonine (○——○); and ecgonine methyl ester (■——■).

Binding inhibition of $^{125}$I benzoylecgonine derivative to ecgonine sheep gamma globulin antiserum by nonradioactive benzoylecgonine sample in 0.01 M phosphate buffered saline (●——●), rabbit plasma (○——○) and human urine (▲——▲).

Standard calibration curves for the detection of benzoylecgonine in human urine with sheep (●——●) and rabbit (○——○) antisera.

Plasma levels of cocaine metabolite(s) in rabbit after i.v. administration of 4 mg of cocaine HCl.

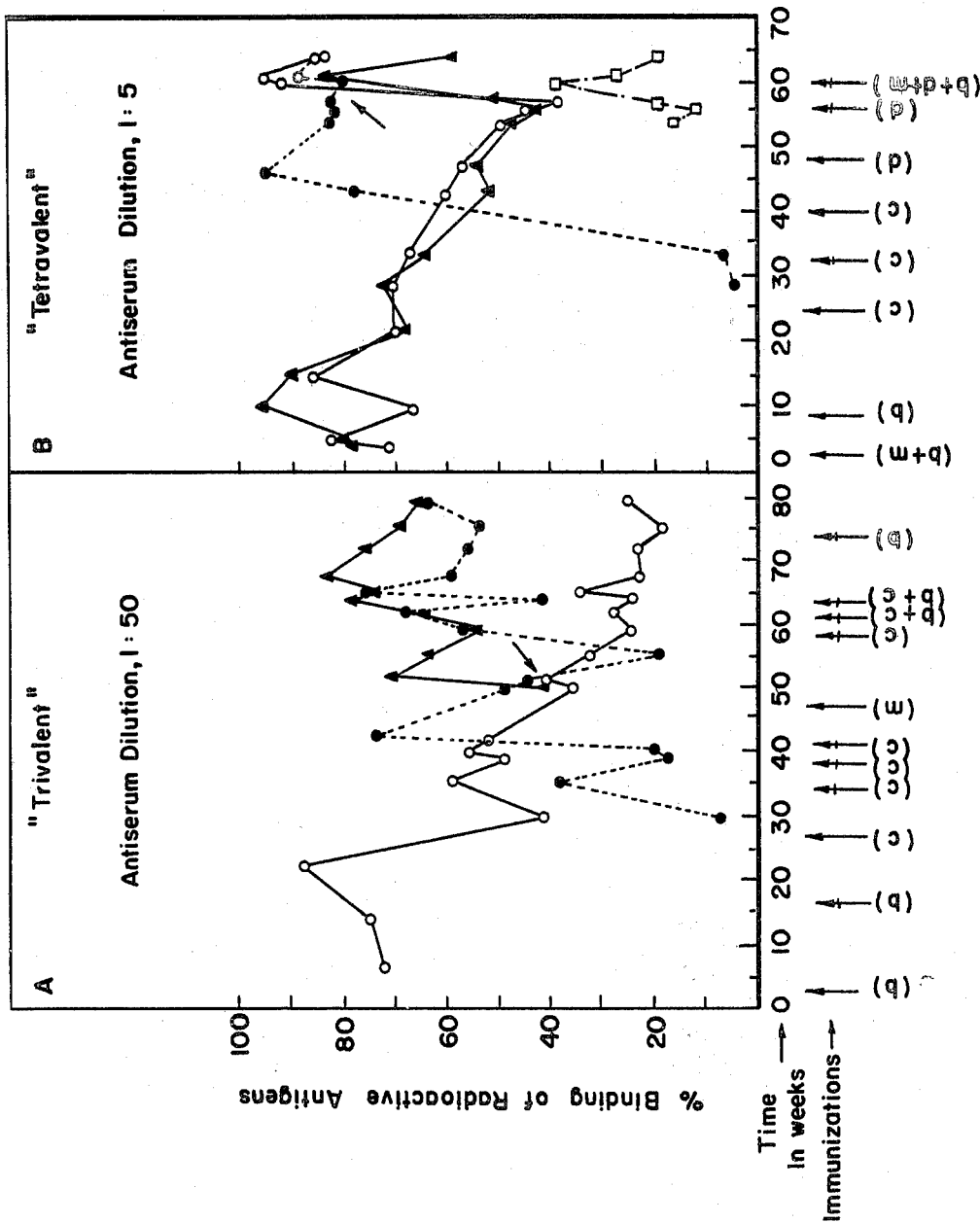

SIMULTANEOUS RADIO IMMUNOASSAY OF MULTIPLE ANTIGENS AND ASSAY FOR COCAINE METABOLITES

This is a division of application Ser. No. 761,078, filed Jan. 21, 1977.

BACKGROUND OF THE INVENTION

The recent upsurge in the degree of drug abuse has led to the necessity for rapid, reliable and efficient methods for detecting the presence of drugs, their metabolites or derivatives in human body fluids such as plasma, urine, etc. In recent years, numerous methods have been developed for the detection of a variety of drugs subject to abuse, such as morphine, barbiturates, amphetamines, lysergide, nicotine, diphenylhydantoin, chloradiazepoxide and cannabinoids.

The following patents describe these methods: U.S. Pat. No. 3,766,162, Spector; U.S. Pat. No. 3,775,536, Spector et al; U.S. Pat. No. 3,799,741, Williams; U.S. Pat. No. 3,882,245, Spector et al; U.S. Pat. No. 3,843,696, Wagner et al; U.S. Pat. No. 3,853,987, Dreyer; U.S. Pat. No. 3,867,366, Rubenstein et al; U.S. Pat. No. 3,878,187, Schneider et al; U.S. Pat. No. 3,879,262, Schuurs et al; U.S. Pat. No. 3,884,898, Schneider; U.S. Pat. No. 3,888,864, Cleeland et al; U.S. Pat. No. 3,952,091, Grunberg et al; U.S. Pat. No. 3,966,744, Goldstein et al; U.S. Pat. No. 3,888,866, Lente et al; and, U.S. Pat. No. 3,690,834, Goldstein et al.

One of the most convenient, efficient and accurate methods for the detection of small amounts of organic compounds in fluids is the so-called radioimmunoassay method. See *Radioimmunoassay Methods*, Churchill, Livingston, London, 1971, and Yalow et al, *Journal of Clinical Investigation*, Vol. 39, pg. 1157, 1960.

Radioimmunoassay (RIA) is a term employed to describe any of several methods for determining small concentrations of substances in biological fluids based on the utilization of radioactively labeled substances which form immuno-chemical complexes with antibodies to that substance. Various RIA techniques are known for measuring concentrations of both antibodies and substances for which there exist antibodies. The RIA of a substance for which there exists antibodies specific to that substance is based on the observation that a known amount of that substance which has been radioactively labeled will compete equally with an unknown amount of that substance which is unlabeled for a limited number of complexing sites on antibodies specific to the substance.

RIA is especially suited for the detection of extremely minute amounts of substances in biological fluids and would, therefore, be extremely valuable in the detection of drugs or their metabolites in the biological fluids of the body. With conventional analytical methods, it is extremely difficult to measure the minute amounts of such metabolites which occur in human body fluids due to the intake of the drugs.

As noted above, RIA procedures are based upon the characteristics that an antibody binds equally to labeled or unlabeled antigen. The concentration of the non-labeled form in the solution determines the relative amount of labeled or non-labeled antigen which will bind to antibody. By maintaining the concentration of antibody and labeled antigen constant and conducting the RIA procedure using a series of known amounts of non-labeled antigen, a standard curve can be constructed. Subsequently, when an unknown amount of antigen in a serum or other biological sample is reacted in the same way, its concentration can be determined by relating the value obtained to the standard curve.

The technique may be represented by the following scheme:

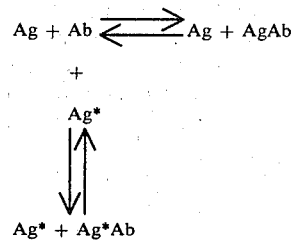

where,
Ag is the antigen to be assayed
Ag* is the labeled antigen and
Ab is the anti body The amount of Ab is arranged to be insufficient to react with all of Ag+Ag*. The amount of Ag* added and Ag present in the standards or the unknown sample will compete for the limited binding sites on Ab. If Ag* is separated from Ag*Ab in the above reaction and the level of activity of each separated part measured, then their individual values or their ratios would be related to the amount of Ag present in the standards or the sample. By the use of standard preparations of Ag, a calibration curve is generated.

To date, however, no completely satisfactory method has been proposed for the radioimmunoassay of cocaine, its derivatives or metabolites in body fluids.

Recent studies have shown that cocaine is rapidly metabolized in man. The principal metabolite that appears in urine is benzoylecgonine (BE) which is found along with smaller amounts of ecgonine (E). Cocaine itself is found in very low concentrations, if at all. Cocaine and its metabolites have been analyzed by thin-layer (TLC) and gas chromatography (GLC) and more recently by the Enzyme Multiplied Immunoassay Technique (EMIT). U.S. Pat. No. 3,888,866 describes a spin label immunoassay for cocaine derivatives.

The major disadvantages associated with TLC, GLC and EMIT assays are their lack of sensitivity and their lack of susceptibility to automation. Moreover, EMIT assays are subject to interference due to enzyme poisons present in many biological specimens, particularly, endogenous lysozyme in some human urine specimens.

A further problem which confronts the art is the screening of body fluids for the presence of multiple drugs. If a subject is suspected of having ingested a drug and no clue whatsoever exists as to the nature of the drug, it could be highly advantageous to be able to "screen" the subject's body fluids for a plurality of drugs in a single test, thereby eliminating the necessity of having to run a series of tests designed only to test for the presence of a single drug. Obviously, the provision of a method for at least qualitatively analyzing a body fluid for the presence of multiple drugs, thereby eliminating the presence of a large number of other drugs, would be more economical and of great benefit in controlling and monitoring of drug abuse.

Immunoassay methods have been proposed for detecting the presence of multiple drugs in body fluids; however, these methods depend upon the production of an anti-serum for each particular drug in a separate donor animal and combining the anti-sera in vitro to produce the necessary reagent for the immunoassay method. To date, no method has been provided which enables the production of an anti-sera for a variety of drugs and/or their derivatives from a single donor animal thereby alleviating the disadvantageous time requirements required for the prior art method. Moreover, the maintenance of large numbers of animals and the attendant expense would be eliminated if the anti-serum were derived from a single animal.

SUMMARY OF THE INVENTION

The present invention is predicated on the discovery that an antigenic conjugate of ecgonine or its acetate and a peptide, protein or polysaccharide elicits anti-benzoylecgonine serum upon immunization of an animal species therewith, said anti-serum being suitable for use in a raioimmunoassay method for the detection of the cocaine metabolite benzoylecgonine in organs and body fluids, particularly human urine.

The invention includes the antigenic conjugates of ecgonine or its acetate and carrier (protein, peptide or polysaccharide); the anti-serum produced by immunization of an animal with said conjugate and the method of preparation of the anti-serum; an immunoassay for cocaine metabolites employing the anti-serum and compositions comprising the anti-serum and labeled antigen (e.g., $I^{125}$ benzoylecgonine) and/or non-labeled benzoylecgonine.

In another embodiment of the invention, anti-sera for a variety of drugs or drug metabolites are produced from a single animal which may be utilized in a method for the screening of multiple drugs (or their metabolites) in biological specimens. This embodiment avoids the "dilution effect" inherent in prior art methods where different specific anti-sera are produced in a number of different animals and then combined for utilization in a screening method.

When the separately produced anti-sera are combined to prepare a polyvalent anti-serum, each is "diluted" by the other thereby lessening the sensitivity of the overall combined reagent.

According to this embodiment of the invention, an anti-serum against several drugs (or their metabolites) is prepared from the same animal and utilized in, for example, a polyvalent radioimmunoassay PV-RIA capable of screening biological specimens for a number of drugs simultaneously in a single assay. Inasmuch as the anti-sera are produced in situ in a single operation, the above-referred to "dilution effect" is avoided.

The invention includes a composition comprising the plural antigenic conjugates; the anti-serum produced by immunization of an animal with the plural conjugates and the method of preparation of the anti-serum; an immunoassay for a plurality of antigens employing the anti-serum and compositions comprising the anti-serum and the corresponding labeled antigens and/or non-labeled antigens.

BRIEF DESCRIPTION OF THE DRAWINGS

FIG. 5 shows percent binding.

DETAILED DESCRIPTION OF THE INVENTION

Figure 1:
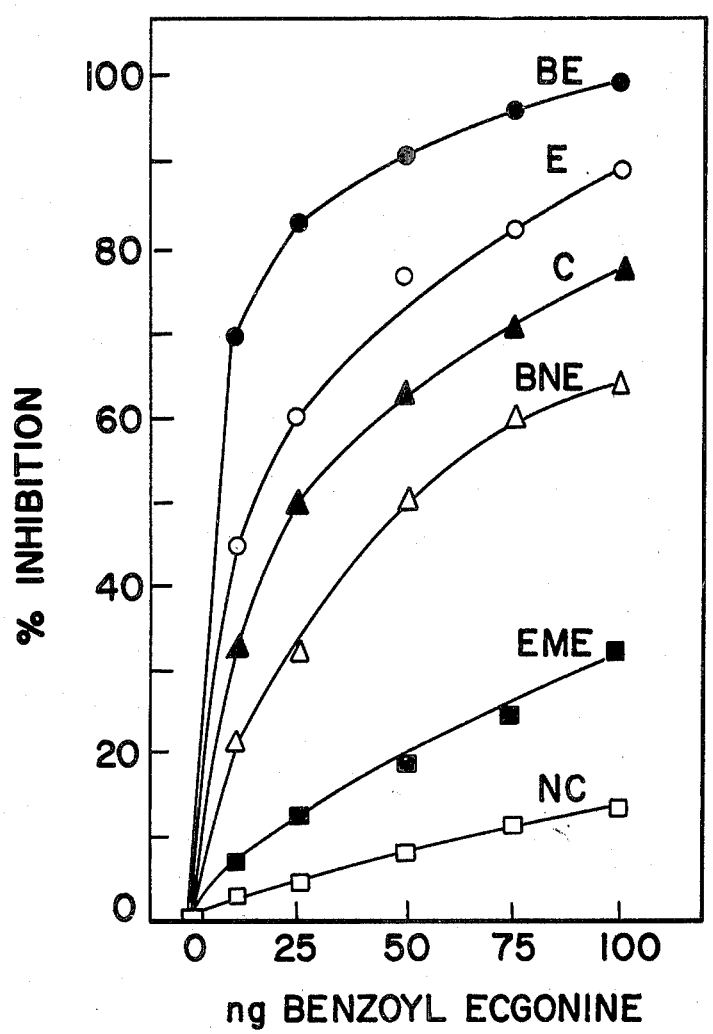
FIGS. 1 and 2 are inhibition curves.

One embodiment of the invention is predicated on the discovery that immunogens prepared by the coupling of ecgonine or its acetate to proteins, peptides or polysaccharides elicit anti-benzoylecgonine serum which is highly specific to benzoylecgonine in an assay for the cocaine metabolite in biological fluids, particularly human urine, thereby providing a highly accurate, efficient and valuable tool for screening subjects for cocaine abuse.

It is most surprising that the ecgonine (or acetate)-carrier immunogen provides an anti-benzoylecgonine serum which is more specific to benzoylecgonine than ecgonine or any of the other cocaine metabolites. It is even further surprising that the ecgonine-carrier immunogen produces a more highly reactive and specific anti-benzoylecgonine serum than the benzoylecgonine-carrier immunogen. Although not wishing to be bound by any theory or mechanism, it is hypothesized that the greater activity to benzoylecgonine suggests a possible conversion of a significant portion of the conjugated ecgonine in the immunogen in vivo to a compound or compounds conformationally more closely related to benzoylecgonine against which the major portion of the total antibodies subsequently elicited was directed.

The antibody elicited by the ecgonine-carrier immunogen recognizes ecgonine about one-half; benzoylnorecgonine about one-fourth; cocaine, nor-cocaine and ecgonine methylester less than about one-tenth as readily as benzoylecgonine, the major cocaine metabolite. With continued periodic boosting, the degree of cocaine and ecgonine reactivity increases but remains below that of benzoylecgonine.

A radioimmunoassay (RIA) method according to the present invention is capable of detecting as little as 5–10 ng of benzoylecgonine, a major cocaine metabolite in human urine, thereby rendering it the most efficient and sensitive method for screening biological fluids for cocaine metabolites perfected to date. The technique enables the monitoring of cocaine intake by man in a relatively simple and highly efficient manner.

It is preferred to employ sheep gamma globulin, bovine or porcine thyroglobulin as the protein carrier for the ecgonine in the preparation of the immunogen. However, it is to be understood that any suitable protein, peptide or polysaccharide (amino sugar containing polysaccharides) may be employed as the carrier.

Specific examples include: bovine, rabbit, pork, sheep or human serum albumin; bovine, rabbit, pork, sheep or human gamma globulin; poly-L-lysine, hemocyanin, etc.

The ecgonine or acetate thereof may be bound to the protein, peptide or polysaccharide carrier by reaction in a suitable reaction medium in the presence of a suitable catalyst such as a water soluble carbodiimide; e.g., 1-ethyl-3-(3-dimethylaminopropyl) carbodiimide HCl, dicyclohexylcarbodiimide, etc.

The ecgonine or acetate forms an amide linkage through the 2-carboxyl group on the ecgonine molecule with the amine groups of the proteins, peptides or amino sugar containing polysaccharides.

Where sheep gamma globulin is employed as the carrier and a carbodiimide as the catalyst, the reaction may be represented:

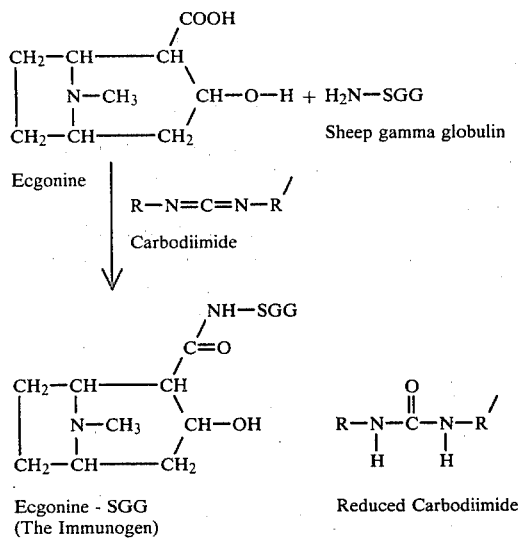

The anti-serum may be prepared by immunization of an animal with the antigenic conjugate followed by bleeding the animal and separating the anti-serum therefrom. Preferably, the antigenic conjugate is dissolved in a saline solution to give a concentration ranging from 1.0 to 4.0 mg/ml. Animals, e.g., horses, rabbits, sheep, goats, etc., may be immunized by injection of the solution such that the animal receives a dose of from about 2 to about 20 mg of the conjugate. Subsequent boosters of smaller amounts of the conjugate may be administered according to any predetermined schedule. As noted above, it could not be predicted that the anti-serum would be specific to benzoylecgonine as opposed to ecgonine from which the conjugate was prepared.

The anti-serum may be utilized in a radioimmunoassay method for the detection of cocaine metabolites in organ homogenates and in biological fluids, particularly human urine. Standard calibration curves may be prepared employing known amounts of anti-serum, radiolabeled benzoylecgonine and non-labeled benzoylecgonine. When utilizing the radioimmunoassay method for analyzing an unknown sample, the values obtained are compared with the calibration curves in order to ascertain the amount of cocaine metabolite in the unknown sample.

It is to be understood that the invention includes compositions comprising the anti-serum and varying amounts of the radiolabeled antigen or the non-labeled antigen for preparing the standard calibration curves for utilization in the radioimmunoassay.

EXAMPLE 1

PREPARATION OF ANTI-BENZOYLECGONINE SERA

Coupling of Ecgonine to Sheep Gamma-Globulin

Eighty mg of ecgonine (E) was added to a solution of 100 mg of sheep gamma-globulin (SGG) in distilled water and stirred until completely dissolved. The pH of the mixture was adjusted to 3.2 with dilute acid and 80 mg of water soluble 1-ethyl-3-(3-dimethylamino propyl) carbodiimide HCl was added. The final reaction mixture was incubated overnight at room temperature (25° C.±2° C.) and then placed in a dialysis bag and dialyzed at 4° C. for one week against two liters of distilled water changed 2-3 times daily. The contents of the bag were assayed by EMIT and the remainder lyophilized.

Immunization, Boosters and Bleeding Schedules

The lyophilized immunogen, ecgonine-sheep gamma-globulin (E-SGG) was dissolved in normal saline to give a solution of 4 mg/ml which was mixed with an equal volume of Freunds' complete adjuvant and emulsified to a thick paste using a blender. Two sheep were each injected with a total of 5 ml of emulsion intramuscularly at four separate sites in the rump and hip, and 2 ml were injected intramuscularly into each of twenty-five Flemish Giant Chinchilla rabbits. Subsequent primary and maintenance boosters were given as described in Table 1.

TABLE 1

| | IMMUNIZATION SCHEDULE OF SHEEP AND RABBITS FOR PREPARATION OF ANTI-BENZOYLECGONINE SERUM | | | | | |
|---|---|---|---|---|---|---|
| Day | Recipient | Type Injection | Wt. Immunogen | Diluent | Total Volume Inj. | Route |
| 0 | Sheep (S) | Primary | 20 mg | Complete Freund Adjuvant | 5.0 ml | I.M. |
|   | Rabbits (R) |  | 2 mg | Complete Freund Adjuvant | 2.0 ml | I.M. |
| 21 | S | Booster I | 10 mg | Incomplete Freund Adjuvant | 5.0 mg | I.M. |
|   | R | Booster I | 1 mg |  | 2.0 ml | I.M. and S.C. |
| 23 | S | Booster II | 10 mg | Incomplete Freund Adjuvant | " | I.M. and S.C. |
|   | R |  | 1 mg |  |  |  |
| 25 | S | Booster III |  |  |  |  |
|   | R |  | 1 mg |  |  |  |
| 28 | BLEED |  |  |  |  |  |

Maintenance boosters given at the previous dose at 4-6 week intervals after the third booster.

Anti-sera

The blood (100-200 ml for sheep and 20-30 ml for rabbits) was obtained from the jugular vein of the sheep and the marginal ear vein of rabbits and held at 37° C. for 2-3 hours, then stored overnight at 4° C. The serum was separated by centrifugation at approximately 3,000 rpm, decanted and stored at −10° C. until used. [It should be noted that the gamma globulin fraction of the anti-serum could be utilized to obtain a relatively more purified antibody].

EXAMPLE 2

Radioimmunoassay

Antigens

One hundred microliters of $I^{125}$-benzoylecgonine derivative (Sp. activity approx. 100 μCi/μg) (Hoffman-LaRoche, Inc., Nutley, N.J.) in phosphate buffered saline (PBS) at pH 7.2, containing 10,000 cpm/100 μl was used in the binding assay. 0.2 ml of the radiotracer was used for qualitative assays and 0.5 ml for quantitative assays.

Radio-chromatography of Radiotracers

To ascertain the purity and chromatographic characteristics of the radioactive tracer, 1-10 μl of the concentrated solution was applied to silica gel-G thin-layer plates. The plates were developed in an ethyl acetate, methanol and ammonium hydroxide (170:20:10) solvent system—I (Davidow et al—American J. Clin., Pathol., 50, 714-719, 1968); chloroform, methanol and ammonia (75:25:5) solvent system—II and Butanol; Acetic acid: Water (4:1:1) solvent III. To locate the various compounds the plates were sprayed first with silver nitrate (or acetate) solution followed by iodoplatinate spray reagent. After location of cocaine (C), ecgonine (E), and benzoylecgonine (BE) on TLC plates, the total developed area was divided into seventeen equal horizontal segments, scrapped individually from the TLC plate and counted for radioactive measurements using a Model MS-588 (Micromedic System, Inc.) gamma counter.

Radioimmunoassay

One-tenth ml aliquots of anti-sera diluted from 1:2 to 1:100 were incubated with $I^{125}$ benzoylecgonine derivative representing approximately 10,000 cpm/100 μl in the presence of either 0.1 ml of normal sheep serum (NSS) or normal rabbit serum (NRS) and sufficient PBS (ph 7.2) was added to each mixture to effect a final volume of 0.5 ml. The mixtures were then incubated at 25° C. for one hour and 0.5 ml of a neutral saturated ammonium sulfate solution was then added to all tubes. The tubes were vortex mixed and the mixture reincubated at 25° C. for 15 minutes. The precipitates obtained after centrifugation at 3,000 rpm for 30 minutes were washed twice with equal volumes of 50% saturated ammonium sulfate. The percent binding of the radioactive tracer was then determined. The dilution of sera from sheep and rabbits that gave 50-70% binding of the radiotracer was selected for the preparation of the standard curve and the screening of biological specimens.

For qualitative screening of human urine specimens, 0.2 ml of the appropriate anti-serum dilution, 0.2 ml of the radiotracer, and 0.1 ml of the varying dilutions of benzoylecgonine, benzoylnorecgonine, ecgonine, ecgonine methylester, cocaine, nor-cocaine, or unknown biological specimen (urine, plasma, organ homogenate) were used in the radioimmunoassay. For quantitative analysis of plasma, urine, or tissue specimens from rabbits and rats, the volume of anti-serum dilution and radioactive tracer was increased to 0.5 ml and the volume of saturated ammonium sulfate to be added was increased to 1.0 ml. This latter procedure provided a standard curve with an extended range of linearity over a concentration range of 0-1000 ng/ml, in contrast to the limited linearity (0-100 mg/ml) for qualitative screening.

Animal Experiments

Control plasma specimens from the marginal ear vein of four New Zealand Albino rabbits which were approximately 3 kg in weight were collected. Two ml of a solution of cocaine hydrochloride (2 mg/ml) in saline was then injected I.V. into each animal. Blood specimens were collected alternately from the marginal ear veins every one to two hours for a total of seven hours and finally at 24 hours for the determination of plasma levels of cocaine metabolites. Four mg of cocaine hydrochloride was administered I.V. to another group of two anesthetized rabbits and hourly urine specimens collected directly from ureters for a total of 6 hours.

Fifty and 20 mg of cocaine hydrochloride were injected I.V. and I.P. into two rabbits and two rats, respectively. After 4 hours the animals were sacrificed and various tissues obtained for analysis.

Human Urines From Drug Abuse Programs

Urines from various clinics located in different parts of the City of New York were routinely analyzed by thin layer chromatograph (TLC). All positive urines for cocaine metabolite by TLC (total specimen 438) and approximately an equal number of randomly obtained TLC negative urines (total specimens 615) were subsequently examined by the EMIT-Cocaine metabolite test and by radioimmunoassay.

Radiochromatography

Mobility (RF) of unlabeled cocaine, nor-cocaine, benzoylecgonine and ecgonine in solvent system I was 0.91, 0.91, 0.05 and 0.00; in solvent system II 0.93; 0.96, 0.48, and 0.08 and in solvent system III—0.38, 0.51, 0.34 and 0.06, respectively. For $I^{125}$ benzoylecgonine derivative over 80% of the radio-activity was at the RF 0.05, 0.08 and 0.35-0.38 in the three solvent systems, respectively. These results defined the chromatographic characteristics of $I^{125}$-benzoylecgonine derivative (Roche Diagnostics).

Antibody Production

All rabbits (25) and both sheep produced anti-sera capable of binding $I^{125}$-benzoylecgonine derivative. The titers obtained in the first bleeding of sheep were quite low while the titers in rabbits on first bleeding were somewhat higher than the sheep. As the immunizing boosters were continued the titers gradually rose until a 1:200 dilution for sheep and 1:500 for rabbit anti-sera were capable of binding 50% of $I^{125}$-benzoylecgonine derivative. Most of the studies reported are with anti-sera which had a titer of over 1:50 for 50% binding. It was observed that relatively steeper slopes of the standard curve are obtained if one works with anti-sera dilution giving 60-70% binding of the radioactive tracer.

The above procedure was repeated utilizing ecgonine acetate-sheep gamma globulin conjugate and ecgonine acetate-bovine thyroglobulin conjugate in rabbits. Titers as high as 1:1000 were obtained.

Sensitivity of Radioimmunoassay

Typical standard curves obtained with varying concentrations of cocaine, benzoylecgonine, benzoylnorecgonine and ecgonine prepared in phosphate buffered saline, pH 7.2, are shown in FIG. 1. From the figure it is evident that benzoylecgonine is the most efficient inhibitor for the assay. At least 2 and 5 times the concentration of cocaine and ecgonine, respectively, with benzoyl norecgonine occupying an intermediate position, are required to produce the same amount of inhibition. With periodic boosting of the animals (e.g., rabbits), the relative inhibition by cocaine and ecgonine increases but remains less than that of benzoylecgonine. Additionally, the detection range of benzoylecgonine, the major cocaine metabolite, appears to be between 2–10 ng/assay tube, the same as reported for most other drug RIA procedures (FIG. 2).

Figure 2:
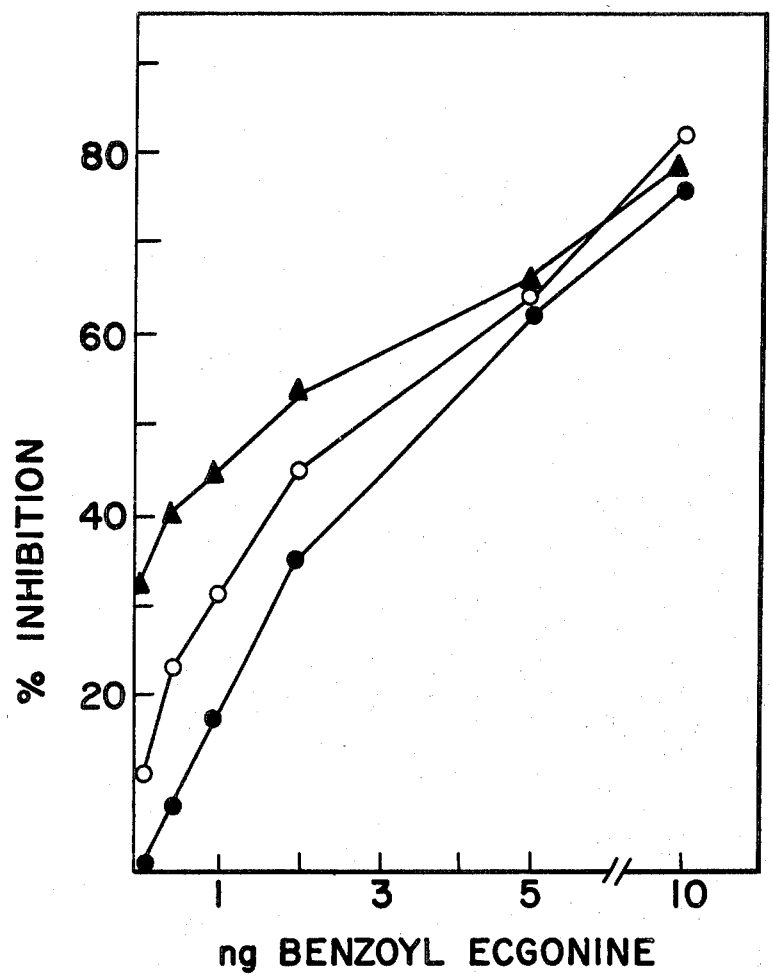

FIG. 2 represents the binding inhibition of $I^{125}$-benzoylecgonine derivative to ecgonine-SGG anti-serum by non-radioactive benzoylecgonine sample in 0.01 M phosphate-buffered saline, rabbit plasma and human urine.

Normal rabbit serum and normal human urines are also seen to demonstrate approximately 10 and 30% non-specific inhibition (FIG. 2). This is apparently due to endogenous materials present in these biological specimens. The non-specific inhibition obtained with concentrated urine can be reduced to less than 5% on dilution of the urine specimen 1:4 with either water or normal saline.

Figure 3:
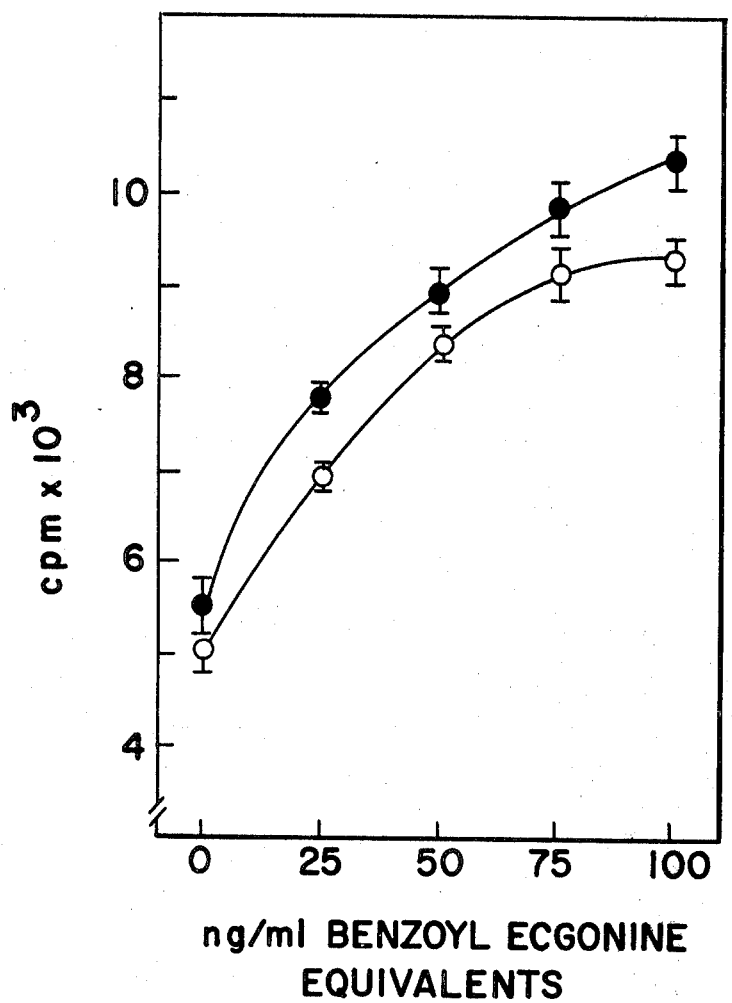
FIGS. 3, 6 and 7 are calibration curves.

FIG. 3 represents standard calibration curves for the detection of benzoylecgonine.

With benzoylecgonine a curvilinear relationship up to 100 ng/ml is evident with 0.2 ml each of the appropriate radiotracer and antibody dilution are used in conjunction with 0.1 ml of the standard solutions (FIG. 3). This type of standard curve was used for routine screening purposes. Beyond the 75 ng/ml concentration a gradual plateauing of the curve is observed. However, the usable "quasi-linear" range can substantially be increased if the volume of the antibody and radiotracer are increased from 0.2 ml to 0.5 ml (FIG. 1). For quantitative analysis therefore it would be desirable to follow the latter procedure.

Specificity

As indicated above, the antibodies produced recognize benzoylecgonine (1.0) most readily followed by ecgonine (0.5) benzoylnorecgonine (0.25) and cocaine (0.15). Norcocaine and ecgonine methylester were least reactive (less than 0.02). There was insignificant cross reactivity with atropine, homotropine and scopalamine which are somewhat structurally related to the tropane portion of the cocaine molecule. A local anesthetic such as procaine, all other major drugs of abuse, including amphetamine, barbiturates, morphine, methadone and about 30 other commonly prescribed and used drugs were also examined and showed insignificant cross reactivity.

Animal Experiments

Figure 4:
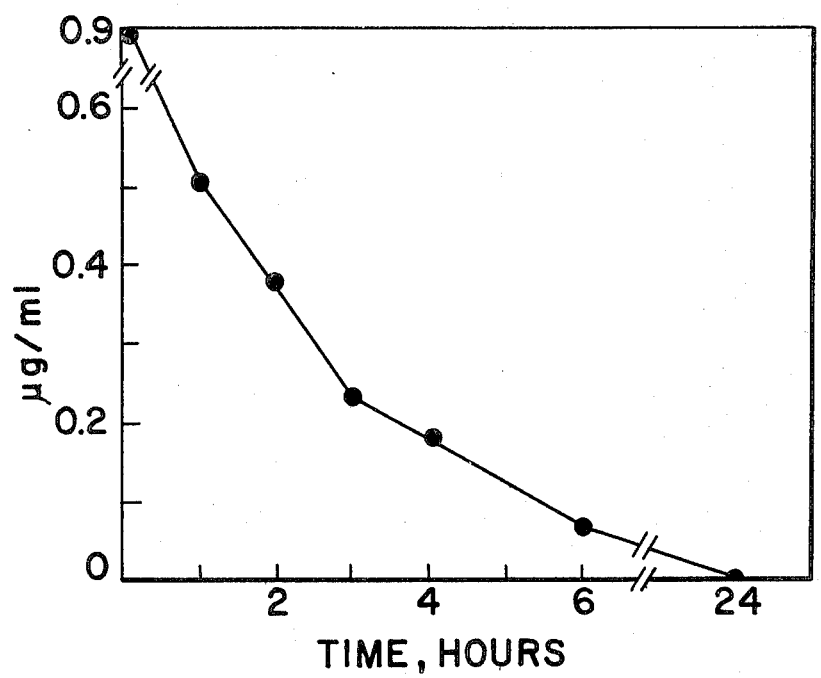
FIG. 4 shows cocaine metalolite levels.

FIG. 4 shows plasma cocaine metabolite levels in rabbits at various time intervals after administration of 4 mg of cocaine-HCl intravenously. The data indicates that there is a rapid decline in plasma levels in the first two hours followed by a relatively slower decline. The plasma half-life of the metabolites in rabbits appears to be 1.8 hr. and none can be detected in plasma after 24 hours when either 4 mg (FIG. 4) of 12 mg of cocaine HCl are administered. The excretion of cocaine metabolites into the urine at various time intervals are presented in Table 2.

TABLE 2

Excretion of Cocaine Metabolite(s) in Urine of Rabbits Receiving 4 mg. of Cocaine HCl Intravenously.

| Time (hr.) | Vol. of Urine | µg/ml | µg Excreted/hr. | Total Excreted (µg) |
|---|---|---|---|---|
| Blank | 31.0 ml | 0.08* | 2.48* | 2.48* |
| 1 hr. | 7.40 ml | 29.37 | 217.34 | 217.34 |
| 2 hrs. | 5.93 ml | 37.60 | 222.97 | 440.31 |
| 3 hrs. | 5.73 ml | 29.97 | 171.73 | 621.04 |
| 4 hrs. | 6.93 ml | 4.33 | 30.01 | 642.05 |
| 5 hrs. | 18.50 ml | 4.42 | 81.77 | 723.82 |
| 6 hrs. | 9.45 ml | 4.35 | 41.11 | 764.93 |

*Biological background levels unrelated to cocaine or its metabolites.

From this data it is apparent that the rate of excretion peaks within three hours and then falls off gradually. The tissue distribution of cocaine metabolites in rabbits and rats that received an overdose of cocaine hydrochloride are presented in Table 3. Highest concentrations were observed in blood, urine and kidney in the case of rabbits. No urine was obtained from the rats. The highest concentration of cocaine metabolites were found in the blood, liver and kidney of rats with smaller amounts in heart, lungs and brain. Higher concentrations of cocaine metabolites were found in rat lung than in rabbit lungs and higher concentrations of metabolites were also found in rat liver than in the rabbit liver.

TABLE 3

Cocaine Metabolite(s) Distribution Levels in Organs and Biological Fluids of Rabbits and Rats 4 hrs. After Receiving 50 and 20 mg of Cocaine Hydrochloride I.V. and I.P. Respectively.

| | Radioimmunoassay Cocaine Metabolite(s) Levels µg/ml (gm) | |
|---|---|---|
| Organs | Rabbit | Rat |
| Urine | 7.47 | none obtained |
| Blood | 8.35 | 4.00 |
| Liver | 0.51 | 0.82 |
| Kidney | 5.88 | 0.42 |
| Brain | 0.10 | 0.09 |
| Heart | 0.46 | 0.28 |
| Lungs | 0.01 | 0.22 |

Human Urines

The results from 1,053 selected urine specimens obtained from different Methadone Maintenance Treatment Program and detoxification clinics in New York City which were tested by various techniques for cocaine metabolites are summarized in Table 4. The total number of samples that were positive by all procedures was 399 (37.9%) whereas the total number of specimens that were negative by all methods was 341 (32.4%). There were 84 (7.9%) samples which were positive with EMIT and RIA but negative by TLC. Ninety-eight (9.3%) samples were positive by RIA but were negative by EMIT and TLC. These differences are most probably due to the relative lack of sensitivity of TLC and EMIT. In addition, there were 27 (2.6%) samples which were positive by TLC and RIA but negative by EMIT. These samples probably represent false negative findings for the EMIT reagent. In addition 92 (8.7%) EMIT positive specimens were negative by both TLC and RIA. Presumably these represent false positive findings for the EMIT reagent. Only 8 (0.8%) of the specimens were negative by RIA and positive by TLC and EMIT. These represent false negative findings for the RIA procedure. In addition 4 (0.4%) of the specimens that were positive by TLC were negative by EMIT and RIA. These probably represent false positive for the TLC procedure.

TABLE 4

Comparative Data on 1,053 Human Urines[1] Analysed by TLC, Emit and Radioimmunoassay

| Total Samples | Method of Analysis | | | % Total |
|---|---|---|---|---|
| | TLC | EMIT | RIA | |
| 399 | + | + | + | 37.9 |
| 341 | − | − | − | 32.4 |
| 98 | − | − | + | 9.3 |
| 92 | − | + | − | 8.7 |
| 84 | − | + | + | 7.9 |
| 27 | + | − | + | 2.6 |
| 8 | + | + | − | 0.8 |
| 4 | + | − | − | 0.4 |

[1]Human urines were selected from Methadone Maintenance Treatment Program clinics. All TLC positives and approximately equal number of TLC negative specimens were picked up randomly.

The invention relates to a radioimmunoassay which is capable of qualitatively and quantitatively determining cocaine metabolites in biological specimens from humans as well as animals. Because the assay can be performed directly on as little as 0.1 ml of specimen it is simple, rapid and adaptable to automation. It also readily lends itself to the detection of cocaine abuse in man and is a sensitive analytical method for animal experiments. Since the parent compound cocaine is not as readily recognized by the antibody as its metabolites, it is very useful for metabolic studies. From the foregoing data it is apparent that the RIA procedure described here is a sensitive and specific screening test which will serve as an efficient and reliable method for detecting cocaine abuse.

There have been several prior attempts to prepare antibodies to cocaine metabolites and the degree of success has been relatively low when compared with anti-sera prepared for other drugs. The present invention demonstrates that ecgonine-sheep gamma globulin conjugate is an effective immunogen which elicits antibody production in most animals immunized. On the other hand, benzoylecgonine with SGG and other carrier proteins failed to produce antibodies in animals used in these experiments.

An unusual characteristic of the antibody produced is that it recognizes benzoylecgonine more readily than it does ecgonine, which was used to produce the anti-sera. It is conceivable that the animals converted a significant portion of the injected hapten portion (ecgonine) of the conjugate (immunogen) to compounds which are conformationally more closely related to benzoylecgonine than to ecgonine. The total antibody population thus produced is probably more closely attuned to the former than to the latter. Moreover, since there is a rapid and almost total metabolism of cocaine to BE and E in humans it is more useful to be able to detect these metabolites than the parent compound.

ASSAY FOR DETECTION OF MULTIPLE ANTIGENS

In many cases of drug abuse, it would be desirable to conduct a single test to screen for the presence of several drugs (or their metabolites) in a body fluid. Such a screening operation would operate to quickly narrow the field so that quick and efficient quantitative tests can be conducted for a small number of drugs rather than conducting a large number of drug tests in a hit-or-miss operation.

According to a further embodiment of the invention, there is provided a composition comprising a plurality of antigenic conjugates which form a multivalent anti-serum upon immunization of an animal therewith, the said multi-valent anti-serum being capable of complexing a plurality of antigens in a simultaneous multiple immunoassay method.

In some instances, it is desirable to assay a biological fluid for multiple materials. For example, in screening subjects for suspected drug abuse, it would be highly desirable to conduct a single radioimmunoassay method which would be capable of detecting simultaneously the presence of two or more compounds which indicate the presence of multiple drugs. Thus, a single test would be required rather than more expensive and time-consuming individual assays for each drug suspected.

In prior art attempts to minimize costs and expedite the analysis of specimens antisera to single drugs have been combined in vitro to produce a multivalent anti-serum. For example, an in vitro bivalent radioimmunoassay has been devised to screen for morphine and barbiturates (Usategui-Gomez et al) Clin. Chem., 21, 1378–1382, 1975); Mule et al, Clin. Chem., 21, 81–86, 1975; and U.S. Pat. No. 3,952,091). These methods suffer from several disadvantages, however. Different animals are required for the production of each anti-serum, thereby contributing to the overall costs of the program. Moreover, the in vitro mixing of the individual antisera must be carefully regulated to ensure the production of multivalent antisera capable of giving reproducible results.

We have found that the immunization of a single animal with a plurality of antigens enables the production of a multi-valent anti-serum which is capable of complexing a plurality of antigens in a biological fluid.

For example, the antigenic conjugate composition may comprise two or more of (1) an antigenic conjugate of ecgonine and a peptide, protein or polysaccharide, (2) an antigenic conjugate of carboxylmethyl morphine and a peptide, protein or polysaccharide, (3) an antigenic conjugate of 5-ethyl-5-(1-carboxyl-n-propyl) barbituric acid and a peptide, protein or polysaccharide, (4) an antigenic conjugate of oxazepam and a peptide, protein or polysaccharide and (5) an antigenic conjugate of nortriptyline or desmethyl imipramine and a peptide, protein or polysaccharide. The multivalent anti-serum produced by the injection of two or more of these antigenic conjugates into a single animal would be capable of complexing two or more of the antigens: (1) benzoylecgonine, ecgonine and cocaine (cocaine and its metabolites), (2) morphine (opiates), (3) secobarbital (barbiturates), (4) diazepam or oxazepam (benzodiazepenes) and (5) amitryptyline (tricyclic anti-depressants) depending upon the particular antigenic conjugates injected into the animal, in a multiple but simultaneous radioimmunoassay of the antigens in a biological fluid.

It has been found that the antigenic conjugates may be injected simultaneously or sequentially into the animal for eliciting the anti-serum. The anti-serum produced according to this method is useful in a simultaneous multiple radioimmunoassay of a plurality of suspected antigens in a biological fluid. The method is particularly valuable in the detection of drug abuse and enables the screening of subjects for a variety of suspected drugs.

The anti-serum is combined with a plurality of radiolabled or non-labled antigens corresponding to the antigen to be detected to prepare standard calibration curves for use in a radioimmunoassay. In the specific examples set forth above, the radiolabeled antigens would comprise (1) $I^{125}$-benzoylecgonine, (2) $I^{125}$ morphine, (3) $I^{125}$ secobarbital, (4) tritiated or $I^{125}$ diazepam, and (5) tritiated or $I^{125}$ amitriptyline or nortriptyline.

The invention also includes the anti-serum produced according to the above-described method and compositions comprising the anti-serum and a plurality of the labeled antigens or a plurality of the non-labeled antigens for setting up calibration curves for employment in an immunoassay method. In the particular examples set forth above, the non-labled antigens would comprise (1) a conjugate of ecgonine (or acetate) and a peptide, protein or polysaccharide, (2) a conjugate of carboxylmethyl morphine and a peptide protein or polysaccharide, (3) a conjugate of 5-ethyl-5-(1-carboxyl-n-propyl) barbituric acid and a peptide, protein or polysaccharide, (4) a conjugate of oxazepam and a peptide, protein or polysaccharide and (5) a conjugate of nortriptyline or desmethyl imipramine and a peptide, protein or polysaccharide.

In a typical experiment a group of rabbits were immunized with drug protein conjugates of compounds related to morphine, barbiturate, cocaine, benzodiazepenes and tricyclic antidepressants. The "polyvalent" anti-sera elicited from the immunized animals were capable of binding opiates, barbiturates, cocaine metabolites, benzodiazepenes and tricyclic antidepressants individually and/or in combination. The anti-body titers for the various drugs ranged from 1:50 to 1:5000.

EXAMPLE 3

Preparation of Immunogens

One hundred mg of bovine serum albumin were dissolved in 20 ml of distilled water and 80 mg of carboxylmethyl morphine were added. The mixture was adjusted to pH 5.5 with dilute alkali and finally 80 mg of water soluble 1-ethyl-3 (3-dimethylaminopropyl) carbodiimide was added. The mixture was incubated overnight at room temperature and the contents transferred to an appropriate length of dialysis tubing and dialyzed at 4° C. against 2 liters of distilled water with 2-3 changes each day. The dialysate was removed from the bag after 5 days and used directly or lyophilized for future use. Prior to immunizations each conjugate was tested by RIA and EMIT for determining the degree of conjugation of the hapten with the protein. For the preparation of an immunogen to barbiturates, rabbit serum albumin was substituted for the bovine serum albumin and 5-ethyl, 5-(1, carboxyl-n-propyl) barbituric acid was used as the hapten in the above procedure. Ecgonine was conjugated with sheep gamma globulin according to the method described in Example 1 to produce antibody to the cocaine metabolite, benzoylecgonine.

Antibodies to Benzodiazepenes were prepared: Ten mg of succinylated oxazepam were dissolved in 5 ml of distilled water and 15 mg of bovine thyroglobulin were added until completely dissolved. The pH of the mixture was adjusted to 4.9 and finally 20 mg of water soluble 1-ethyl-3 (3-dimethylaminopropyl) carbodiimide HCl were added. The final reaction mixture was incubated overnight at room temperature and then placed in a dialysis bag and dialyzed at 4° C. for 5 days against two liters of distilled water changed 2-3 times daily. The contents of the bag were lyophilized and 10 mg of the immunogen were dissolved in 1.25 ml of normal saline and mixed with an equal volume of Freund's complete adjuvant and emulsified to a thick paste using a syringe. Four rabbits were each injected with a total 0.5 ml of the emulsion intradermally into multiple sites on the flank of the animal using approximately 50 µl at each site. Concomitantly with the immunogen, either 0.5 ml of diphtheria-pertussis-tetanus or pertussis vaccine was administered separately in a different site to enhance the immunologic response of the animals. Subsequent maintenance boosters were given every 6-8 weeks. Twenty to thirty ml of blood were obtained four weeks after the primary immunization from the marginal ear vein of rabbits and serum separated for titer determination. The succinylated derivative is employed to provide carboxyl sites for conjugation. Any low molecular weight dicarboxylic acid may be employed, however.

Antibodies to tricyclic antidepressants were prepared: Fifty mg each of nortriptyline hydrochloride (NT) and desmethylimipramine (DMI) were dissolved in 4 ml of dry pyridine and 20 mg of succinic anhydride were added with stirring until dissolved. The mixture was incubated overnight at room temperature followed by drying under a stream of nitrogen. The two residues remaining were the succinylated derivatives and were redissolved in 2 ml of dioxane each and 5-10 µl aliquots were examined on fluorescent silica gel thin layer plates (TLC) for monitoring the disappearance of the starting materials. In the case of succinylated nortriptyline the remaining portion was added to a separate solution composed of 54 mg of bovine serum albumin (or bovine thyroglobulin) dissolved in 20 ml of a 0.05 M phosphate-buffered saline (PBS) pH 7.8. To this solution was added 190 mg of water soluble 1-ethyl-3 (3-dimethylaminopropyl) carbodiimide HCL until dissolved. The final reaction mixture was incubated overnight at room temperature. The free and the conjugated succinylated derivative was separated by passing the solution through a 25 cm, 1.5 cm diameter glass column filled with a slurry of sephadex G-50 (7 gm/100 ml PBS) and eluting with PBS. Two ml fractions were collected and protein peaks as measured at 260-280 nm which appeared in fractions 11-18 were collected for use to immunize the animals. Eight fractions (total volume 16 ml) representing approximately 50 mg of protein each from NT and DMI conjugates were lyophilized.

In case of succinylated DMI, approximately 50 mg were dissolved in 10 ml of distilled water and to this 50 mg of bovine thyroglobulin were added. The pH of the mixture was 5.7 and finally 60 mg of the above water soluble carbodiimide was added. Incubation and dialysis was performed according to the method described above.

One and a half mg of the conjugate was dissolved in 0.5 ml normal saline and was mixed and emulsified with 0.5 ml of complete Freund's adjuvant and administered according to the technique as previously described. The animals were bled 4 weeks after the primary immunization via the central ear artery for determination of the individual titers. The first bleeding was followed by intramuscular boosters of the respective conjugate dissolved in normal saline and administered every 4-6 weeks until desirable titers were obtained.

Again, any low molecular weight dicarboxylic acid may be substituted for the succinic acid employed above.

Animals may be immunized with these drug-protein conjugates (immunogens) sequentially or simultaneously.

Immunization

One group of rabbits was sequentially immunized intramuscularly with 2 mg of the individual immunogens and another group with the triple (morphine, barbiturate and cocaine) immunogens emulsified in complete Freund's Adjuvant. In the sequential method the second immunogen ws not administered to the animal until the titer for the first one was at least 1:10 (based on 50% binding for the respective radioactive tracer) and the third one was not injected until the "bivalent" antisera for first and second drug immunogens had a minimal titer of 1:10. A fourth immunogen, namely, oxazepam, amitriptylene or desmethylimipramine was administered in a few selected animals having low titers for the first three drugs. In the simultaneous method, the triple immunogen was administered intradermally into multiple sites on the flank of the animal approximately 50 $\mu$l at each site. Concomittantly with the immunogen, 0.5 ml of DPT vaccine was also administered separately at different sites to enhance the immunological response of the animals. Booster injections of 1 mg of the immunogens dissolved in phosphate buffered saline were given at 6-8 weeks intervals after the primary series of injections. Diazepam immunogen was administered intradermally at multiple sites into two of the rabbits to produce a tetravalent antibody. Pertussis vaccine (0.5 ml) was injected separately in other sites to enhance the immunologic response in these two animals. For example, FIG. 5 depicts two of the above-described immunization schedules and drug combinations.

Iodinated ($I^{125}$)-labeled morphine, secobarbital, benzoylecgonine, tritiated diazepam amitriptyline or nortriptyline were used as radiotracers. When anti-sera that was capable of binding 2, 3 or 4 different radioactively labeled drugs were obtained, individual calibration curves were prepared for each drug.

Figures 6A, 6B, 6C, 6D:
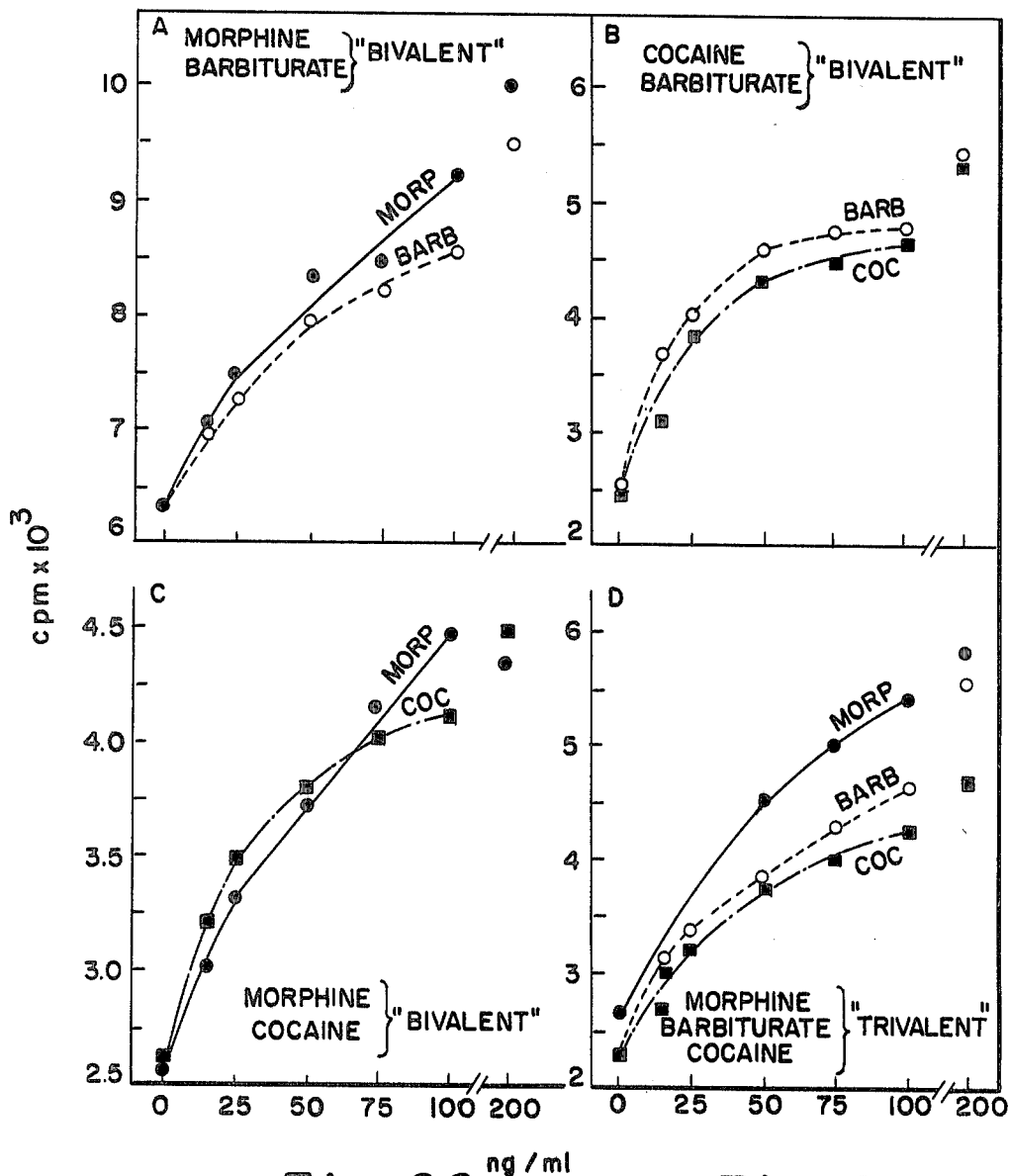
Figure 7B:
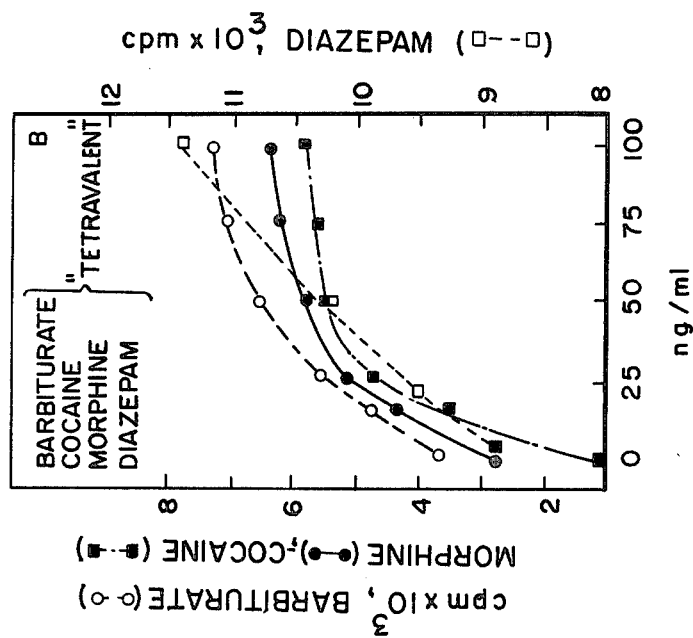
Figure 7A:
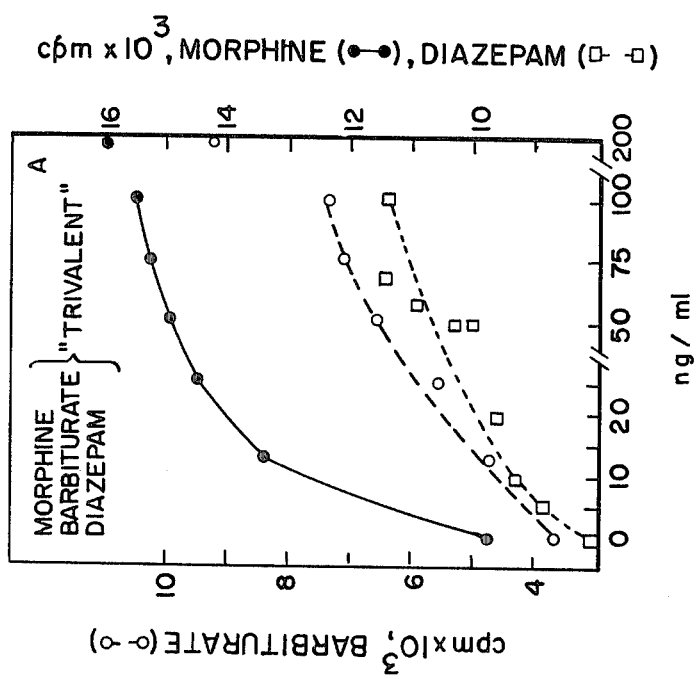

FIGS. 6 and 7 show typical calibration curves for "tetravalent", "trivalent", "bivalent" and "univalent" anti-sera. Because it is possible to vary the relative ratios of the three iodinated antigens in the triple assay, experiments were done to determine the appropriate ratios of the antigens that had to be mixed to obtain similar calibration curves.

Radioimmunoassay

For screening purposes equal volumes of the appropriate radiotracer mixture and appropriate "polyvalent" antiserum dilution were mixed and stabilized overnight at 10° C. to give a "polyvalent" radioimmunoassay (PV-RIA) reagent. It is to be understood that overnight stabilization is not essential; however, the slopes of the calibration curves obtained without stabilization would vary from those obtained after stabilization. Standard solutions ranging from 0-200 ng/ml of morphine sulfate, secobarbital, benzoylecgonine and diazepam were prepared in pooled normal urine. The standard solutions and 1,000 human urine specimens obtained from the Methadone Maintenance Treatment Program Clinics located in various boroughs of the City of New York were randomly screened by the univalent, bivalent and trivalent assays using an automated Micromedic High Speed Pippetting Station (ASP). In addition, 25 selected specimens were also screened by the tetravalent assay. Specimens showing disagreement of results between polyvalent assays were also tested with EMIT reagents. Four tenths ml of the univalent or PV-RIA reagent and 0.1 ml of the undiluted urine specimens were mixed by the APS and incubated for 30 minutes at room temperature. Five-tenths of a saturated ammonium sulfate solution was added to each tube, vortex mixed and the mixtures reincubated for 15 minutes. The sample tubes were then centrifuged for 15 minutes at 3,000 rpm and 0.5 ml of the supernatant removed plus an equal volume of distilled water to wash the residual radioactivity in the lines. The samples were then counted on a Searle Analytical gamma counter (Model 1285-Z). The assay could also be performed by mixing the biological specimen, antibody and the radiotracer in sequence and incubating for 15 minutes. Incubation time can be altered from a minimum of 15 minutes to a maximum of 60 minutes.

The cut-off point (lowest drug concentration) for reporting a "positive" finding for the triple assay (FIG. 6-D) was at 4225 cpm (equivalent to 75 ng/ml of barbiturate, 100 ng/ml of benzoylecgonine and 40 ng/ml for morphine). The same cut-off values were used for the univalent assay for comparison purposes. FIGS. 6-A, B and C shows the calibration curves for various bivalent radioimmunoassays. The bivalent assays were performed prior to the induction of trivalent and tetravalent antibodies in the same animals. For the quadruple assay (FIG. 7-B) 5500 cpm corresponding to approximately 25 ng/ml of morphine and barbiturate and 50 ng/ml of benzoyl ecgonine were used as a cut-off point for screening specimens for these drugs. For diazepam, 10,540 cpm corresponding to about 50 ng/ml were also used as a cut-off point for the detection of positive specimens. It is evident from the calibration curves that ideally all the calibration curves should have identical slopes and avidity for selecting a common concentration for cut-off values. However, calibration curves with different curvilinearity can also be used. In these cases, the detection limits for the various drugs will differ. For an exclusion test, different cut-off points for various drugs would be considered acceptable. The results from univalent and trivalent assays were compared to determine the performance of the latter (Table 5). Out of 1,000 specimens there were 14.5% false positives and 0.4% false negatives by the trivalent assay when compared with the results from the univalent assay. For an exclusion test, these values are considered within acceptable limits. The applicability of the PV-RIA procedure as compared with univalent-RIA is demonstrated by a sensitivity of 99.6% [569/571×100] and a specificity of 85.5% [367/429×100]. As will be seen from results set forth below, a quadrivalent RIA gave equally satisfactory results.

The same principle may also be applied to multiple immunoassays for a variety of antigens in other areas.

TABLE 5

Human Urines from 1,000 Subjects from Methadone Maintenance Treatment program and Detoxification Clinics Tested by Univalent and Trivalent Radioimmunoassays*

| | Univalent | | | |
|---|---|---|---|---|
| No. of Samples | Barbiturate | Cocaine Metabolite | Morphine | Trivalent Assay |
| 367 | − | − | − | − |
| 12 | + | + | + | + |
| 9 | + | + | − | + |

TABLE 5-continued

Human Urines from 1,000 Subjects from Methadone Maintenance Treatment program and Detoxification Clinics Tested by Univalent and Trivalent Radioimmunoassays*

| No. of Samples | Univalent Barbiturate | Cocaine Metabolite | Morphine | Trivalent Assay |
|---|---|---|---|---|
| 36 | + | − | + | + |
| 109 | − | + | + | + |
| 66 | + | − | − | + |
| 70 | − | + | − | + |
| 267 | − | − | + | + |
| Sub Total 569 | | | | |
| 62 | − | − | − | + |
| 1 | + | − | − | − |
| 1 | − | + | − | − |
| Sub Total 64 | | | | |
| TOTAL 1,000 | | | | |

*A sample was considered positive if it contained >75 ng/ml of barbiturate, >100 ng/ml of cocaine and >40 ng/ml of morphine.

EXAMPLE 4

Clinical Testing Procedures

The above 1,000 randomly collected urine specimens from the Methadone Maintenance Treatment Program Clinics and Detoxification Clinics of New York City were also screened by routine thin layer chromatography. According to the Davidow procedure (Amer. J. Clin. Pathol., 50, 714–719, 1968). Specimens showing disagreement of results between univalent and polyvalent assays were also tested with EMIT reagents (Rubenstein et al, Biochem. Biophys. Res. Comm. 47, 846–851, 1972) for the presence of opiates barbiturates and cocaine metabolites. The results were then compared with those obtained according to the above univalent, bivalent and trivalent RIA procedures.

Twenty-five urines were selected based on their thin layer chromatography findings for a quadruple RIA test. Twelve specimens contained only one of the four drugs, 11 contained two or more drugs and two contained none of these drugs.

Animal Organ Homogenates

Twelve rats weighing approximately 300 gm were injected intraperitoneally with varying amounts of d-amphetamine, barbiturate, cocaine, methadone and diazepam either alone or in different combinations. Two of the animals received none of the above drugs. Two hours after administration of the various drug(s), the animals were sacrificed and various organs, urine and blood collected. Organ homogenates, blood and urines were subjected to the univalent and trivalent (morphine-barbiturate-cocaine metabolite) RIA procedure. It was not possible to collect sufficient blood and/or urine on all the animals for use in both univalent and trivalent assays.

As noted above, three hundred sixty-seven of the thousand specimens that were negative by all three univalent RIA techniques were also negative by trivalent RIA. Five hundred sixty-nine specimens were positive by one or more of the univalent assays and were also positive by the triple assay. Of the remaining 64 specimens, 62 were negative by the individual RIA's but were positive by the trivalent RIA.

Out of these 62 specimens, 42 were also negative by EMIT and TLC procedures, ten were positive by TLC, five were positive by EMIT and five positive by both the EMIT and TLC procedures. There were two specimens that were positive for the univalent RIA (one for barbiturate and one for cocaine metabolite) that were negative by trivalent RIA. These specimens would represent false negative for trivalent RIA. If the trivalent assay is compared to the combined results of the univalent RIA, EMIT and TLC then only 42 false positive and no false negatives were found.

The comparative results obtained with 25 selected specimens tested by univalent and tetravalent are presented in Table 6. The data indicates that a tetravalent RIA for screening urine specimens for four drugs simultaneously is feasible.

TABLE 6

Comparison of Results on 25 Selected Human Urines from Drug Abuse Program Tested by Univalent and Tetravalent Radioimmunoassays

| No. of Samples | Univalent Barbiturate | Cocaine Metabolites | Morphine | Diazepam | Tetravalent Assay |
|---|---|---|---|---|---|
| 2 | − | − | − | − | − |
| 3 | + | − | − | − | + |
| 3 | − | + | − | − | + |
| 2 | − | − | + | − | + |
| 4 | − | − | − | + | + |
| 2 | + | + | + | − | + |
| 3 | + | − | + | − | + |
| 2 | + | + | − | − | + |
| 3 | − | + | + | − | + |
| 1 | − | − | + | + | + | off Values: Barbiturate, Morphine 25 ng/ml
Cocaine metabolite, Diazepam = 50 ng/ml

Animal Organo Homogenates

The results obtained in univalent and trivalent radioimmunoassays performed on organ homogenates and biological fluids of rats that had received either one, two, three drugs or none at all are presented in Table 7. The data indicates that whenever a drug, either alone or in combination, was detected by the univalent radioimmunoassay, it was also detected by the trivalent procedure (i.e., animals 1 through 7). When no drugs or non-related drugs were administered to rats, neither the univalent nor the trivalent radioimmunoassay procedures were positive (i.e., animals 8 through 12). In a few instances where lower levels of drug were administered to animals (numbers 4, 5 and 7), univalent assays were negative when the cut off values of 25 ng/ml morphine and 50 ng/ml for cocaine were used. Had a cut off value of 12.5 ng/ml and 25 ng/ml, respectively, been used, these univalent assays would have been considered positive.

| Animal # | Drug and Dose Administered | Specimen | Univalent Barb | Coc$^c$ | Morph | Trivalent Morph-Barb-Coc$^c$ | Animal # | Drug and Dose Administered | Specimen | Univalent Barb | Coc$^c$ | Morph | Morph-Barb-Coc |
|---|---|---|---|---|---|---|---|---|---|---|---|---|---|
| 1 | Cocaine-HCl (0.6 mg/kg) | Brain | − | − | − | − | 5 | Cocaine-HCl (0.3 mg/kg) + Phenobarb-Na | Brain | + | − | − | + |
| | | Kidney | − | + | − | + | | | Kidney | + | − | − | + |
| | | Liver | − | + | − | + | | | Liver | + | − | − | + |
| | | Blood | QNS | QNS | QNS | + | | | Blood | QNS | QNS | QNS | + |

-continued

| Animal # | Drug and Dose Administered | Specimen | Univalent Barb | Univalent Coc[c] | Univalent Morph | Trivalent Morph-Barb-Coc[c] | Animal # | Drug and Dose Administered | Specimen | Univalent Barb | Univalent Coc[c] | Univalent Morph | Morph-Barb-Coc |
|---|---|---|---|---|---|---|---|---|---|---|---|---|---|
| 2 | Phenobarb-Na (2 mg/kg) | Brain | + | − | − | + | 6 | (1 mg/kg) Morphine-SO$_4$ (0.5 mg/kg) + Cocaine-HCl (0.3 mg/kg) | Brain | − | − | − | + |
|  |  | Kidney | + | − | − | + |  |  | Kidney | − | + | + | + |
|  |  | Liver | + | − | − | + |  |  | Liver | − | + | + | + |
|  |  | Blood | QNS | QNS | QNS | + |  |  | Blood | QNS | QNS | QNS | + |
|  |  |  |  |  |  |  |  |  | Urine | QNS | QNS | QNS | + |
| 3 | Morphine-SO$_4$ (1 mg/kg) | Brain | − | − | − | − | 7 | Morphine-SO$_4$ (0.3 mg/kg) Phenobarb-Na (0.7 mg/kg) Cocaine-HCl (0.2 mg/kg) | Brain | + | − | − | + |
|  |  | Kidney | − | − | + | + |  |  | Kidney | + | − | + | + |
|  |  | Liver | − | − | + | + |  |  | Liver | + | + | − | + |
|  |  | Blood | − | − | + | + |  |  | Blood | QNS | QNS | QNS | + |
|  |  | Urine | QNS | QNS | QNS | + |  |  | Urine | QNS | QNS | QNS | + |
| 4 | Morphine-SO$_4$ (0.5 mg/kg) + Phenobarb-Na (1 mg/kg) | Brain | + | − | − | + | 8 | Amphetamine-HCl (0.1 mg/kg) | Brain | − | − | − | − |
|  |  | Kidney | + | − | + | + |  |  |  |  |  |  |  |
|  |  | Liver | + | − | − | + |  |  |  |  |  |  |  |
|  |  | Blood | QNS | QNS | QNS | + | 9 | Methadone-SO$_4$ (0.6 mg/kg) | Kidney | − | − | − | − |
|  |  | Urine | QNS | QNS | QNS | + | 10 | Diazepam (0.04 mg/kg) | Liver | − | − | − | − |
|  |  |  |  |  |  |  | 11, 12 | Saline (no drugs) | Blood | QNS | QNS | QNS | − |

[a]Cut off Value: Barbiturate and Cocaine - 50 ng/ml Morphine - 25 ng/ml
[b]Sacrificed 2 hrs. after drug administration
[c]Cocaine metabolite measured as benzoylecgonine equivalents
QNS = quantity Not Sufficient to Test As noted above, the applicability of the polyvalent RIA procedure as compared with the univalent procedure is demonstrated by a sensitivity of 99.6% (569/571×100) and a specificity of 85.5% (367/429×100). The false positive and false negative rates, namely 14.5% and 0.4%, respectively, are considered within acceptable limits for screening purposes. It should be noted that most of the presumably false positive findings may in fact be due to drugs which were below the cut off value for an individual drug but were above the trivalent RIA cut off value by an additive effect.

In most laboratories and major drug abuse programs, approximately 80% of the clinical specimens are negative for the major drugs subject to abuse. The polyvalent RIA described could serve as an exclusion test assay for such drugs. By eliminating approximately 80% of the specimens from further consideration, substantial savings in time and expense could be achieved. The exclusion procedure could also be used in screening forensic toxicology specimens where major drug classes could be ruled out by a simple polyvalent immunoassay screen of organ homogenates and biological fluids.

Even though it is possible to prepare a polyvalent antibody by in vitro mixing of univalent antisera from different animals, the preparation of a polyvalent antisera in the same animal produces more uniform antisera and requires fewer animals for antibody preparation. Since fewer animals are required, there is also less chance that the serum of a particular animal in the pooled sera will cause untoward reactions. An additional advantage of the in vivo polyvalent anti-sera is that the potency of a low titered component(s), i.e., cocaine and/or diazepam, will not be further reduced by in vitro mixing.

In sequential immunization procedures described above and depicted in FIG. 5 nearly all animals produced antibodies to both morphine and barbiturates. Approximately one-half of the animals that had responded to the two immunogens also responded to the third (i.e., cocaine metabolite) (FIG. 5A). Two of the rabbits that had responded to all three immunogens were subsequently inoculated with the fourth (i.e., diazepam) (FIG. 5B). At 1-2 or 1-5 dilution slopes of the calibration curves were adequate for use in quadruple RIA. Another group of two animals with morphine barbiturate-cocaine metabolite antibodies were subsequently inoculated with the fourth (i.e., amitriptyline) immunogen.

Ideally each constituent of a polyvalent antiserum should have similar binding properties so that a single dilution would be appropriate for all of the individual components (see arrows FIG. 5). For the simultaneous "triple immunizations" three of four animals produced anti-sera capable of binding the three drugs to varying degrees, suggesting that both sequential and simultaneous immunization procedures could be utilized.

Ideally the calibration curves for the various drugs should have identical slopes. FIGS. 6 and 7 show typical calibration curves for various polyvalent radioimmunoassays obtained by a single dilution of the various anti-sera. In general, the slopes of the individual calibration curves in the multiple RIA's were flatter than if they were prepared by single RIA's. In some animals it was not practical to optimally dilute the antiserum for each drug, because the titers and slopes of the calibration curves for the three or four drugs were significantly different. The calibration curves obtained with these reagents had somewhat different slopes. Consequently, the detection limits for the drugs varies. By appropriate scheduling of the booster injections, it is possible to obtain polyvalent antisera which would provide optimal binding for all drugs at a single dilution.

Theoretically, the capability of animals to produce antibodies to multiple antigens is unlimited as long as the antigens are not chemically related. For most purposes, however, it would not be practical to utilize the same animal for more than about ten, preferably five, antigens.

The radiolabelled compounds utilized according to the present invention may be prepared according to well known and/or readily available methods. See, for example, Davis et al, Clin. Chem. 21/10, pp. 1498-1505 (1975). See also $^{14}C$, $^{3}H$, $^{125}I$ and $^{35}S$ Labelled Drugs, New England Nuclear, September, 1976. It is also to be understood that drugs (or derivatives thereof) labelled with enzymes, free radicals, sensitized red blood cells, etc. may also be employed in applicable immunoassays.

While the above description has been limited to a discussion of radioimmunoassay procedures, it is to be understood that the principles of this invention are applicable to other immunoassays such as EMIT, FRAT, HI, etc.

Reference may be had to the following for descriptions of various methods and reagents employed in practicing the present invention: Spector et al, Science, Vol. 168, pp. 1347-48, June 12, 1970; Spector et al, Science, Vol. 174, pp. 1037-1039, Dec. 3, 1971; Peskar, Jour. Pharm. Exp. Therap., Vol. 186, pp. 167-168 (1973); Dixon et al, Jour. Pharm. Sci., Vol. 64, pp. 937-38 (1975); Cleeland et al, Clin. Chem., 2216, pp. 712-725, (1976); Aherne, Br. J. Clin, Pharmac. Vol. 3, pp. 561-65 (1976); Satoh et al, J. Biochem., Vol. 73, pp. 1115-18 (1973); Satoh et al, J. Biochem., Vol. 75, p. 1302.

What is claimed is:

1. In an immunoassay method for the detection of a cocaine metabolite in a biological tissue or fluid wherein an anti-serum is combined with said biological tissue or fluid to form a complex with said cocaine metabolite, said complex being detectable in an assay, the improvement comprising employing an anti-benzoylecgonine serum produced by immunizing an animal by injecting into said animal an antigenic conjugate of ecgonine or the acetate thereof and a peptide, protein or polysaccharide and eliciting serum from said animal.

2. The immunoassay method of claim 1 wherein said conjugate is a conjugate of ecgonine and sheep gamma-globulin.

3. A composition suitable for use in an immunoassay method for detecting a cocaine metabolite in a biological tissue or fluid comprising an antibenzoylecgonine serum and a labeled benzoylecgonine, wherein said anti-benzoylecgonine serum is produced by immunizing an animal by injecting into said animal an antigenic conjugate of ecgonine or the acetate thereof and a peptide, protein or polysaccharide and eliciting serum from said animal.

4. The composition of claim 3 wherein said labeled benzoylecgonine is $I^{125}$-benzoylecgonine derivative.

5. The composition of claim 4 wherein said antiserum is produced employing an antigenic conjugate of ecgonine or the acetate thereof and a gamma globulin or a thyroglobulin.

6. The composition of claim 5 wherein said antiserum is produced employing an antigenic conjugate of ecgonine and sheep gamma globulin.

7. A composition comprising anti-benzoylecgonine serum and benzoylecgonine wherein said anti-benzoylecgonine serum is produced by immunizing an animal by injecting into said animal an antigenic conjugate of ecgonine or the acetate thereof and a peptide protein or polysaccharide and eliciting serum from said animal.

8. The composition of claim 7 wherein said antiserum is produced employing an antigenic conjugate of ecgonine or an acetate thereof and a gamma globulin or a thyroglobulin.

9. The composition of claim 7 wherein said antiserum is produced employing an antigenic conjugate of ecgonine and sheep gamma globulin.

* * * * *